(12) United States Patent
Miki et al.

(10) Patent No.: US 6,753,431 B2
(45) Date of Patent: Jun. 22, 2004

(54) PRODUCTION OF MIXED ACID ANHYDRIDE AND AMIDE COMPOUND

(75) Inventors: Takashi Miki, Ibaraki (JP); Hideki Ushio, Takatsuki (JP); Isao Kurimoto, Suita (JP)

(73) Assignee: Sumitomo Chemical Company Limited, Osaka (JP)

( * ) Notice: Subject to any disclaimer, the term of this patent is extended or adjusted under 35 U.S.C. 154(b) by 0 days.

(21) Appl. No.: 09/870,676

(22) Filed: Jun. 1, 2001

(65) Prior Publication Data

US 2002/0032346 A1 Mar. 14, 2002

(30) Foreign Application Priority Data

Jun. 2, 2000 (JP) ........................................ 2000-165748

(51) Int. Cl.$^7$ ..................... C07D 211/22; C07D 211/60; C07F 9/22; C07F 9/28; C07C 269/00
(52) U.S. Cl. ..................... 546/221; 546/245; 548/112; 548/119; 548/201; 548/206; 548/235; 548/237; 548/334.5; 548/413; 548/532; 548/953; 548/956; 548/966; 562/24; 562/879; 562/887; 562/888; 562/897
(58) Field of Search .......................... 562/24, 879, 887; 562/888, 897; 546/221, 245; 548/112, 119, 413, 532, 953, 956, 966, 201, 206, 235, 237, 334.5; 423/304, 512.1; 554/88, 154, 164

(56) References Cited

U.S. PATENT DOCUMENTS

| 3,264,281 A | 8/1966 | Applewhite et al. |
| 3,640,991 A | 2/1972 | Callahan |
| 4,874,558 A | * 10/1989 | Fife et al. ................... 562/894 |

FOREIGN PATENT DOCUMENTS

| GB | 2 078 724 A | 1/1982 |
| JP | 6-184054 | 7/1994 |
| JP | 10-175955 | 6/1998 |

OTHER PUBLICATIONS

Webster's II New Riverside University Dictionary, p. 77 (definition of "add") and p. 1160 (definition of "sum"). Houghton MIfflin Company (1994).*
Ramage et al, "A Kinetic Study of Phosphinic Carboxylic Mixed Anhydrides" J. Chem. Soc. Perkin Trans. I, pp. 1617–1622 (1985).*
Benoiton et al, "Preparation of activated esters of N–alkoxycarbonylamino and other acids by modification of the mixed anhydride procedure" J. Peptide Protein Res. vol. 42, pp. 278–283 (1993).*
E.J. Bourne et al, Journal of the American Chemical Society. pp. 2006–2012 (1954).*
Urbanski et al, Polish Journal of Chemistry, vol. 58, pp. 1227–1229 (1984).*
Gaede, B., Organic Process Research and Development, vol. 3, pp. 92–93 (1999).*
T. Applewhite et al., "Suppression of Racemization During Peptide Syntheses", Tetrahedron Letters, No. 15, pp. 819–825.
G. Anderson et al., "A Reinvestigation of the Mixed Carbonic Anhydride Method of Peptide Synthesis", Journal of the American Chemical Society, (Sep. 13, 1967), pp. 5012–5017.
N. Albertson, "Synthesis of Peptides with Mixed Anhydrides", Organic Reactions, vol. 12, (1962), pp. 157–355.

* cited by examiner

Primary Examiner—Richard L. Raymond
Assistant Examiner—Zachary C. Tucker
(74) Attorney, Agent, or Firm—Sughrue Mion, PLLC

(57) ABSTRACT

There is disclosed an advantageous mixed acid anhydride production method of formula (1):

$$R^1C(O)OY(O)_n(R^2)_p \qquad (1)$$

wherein $R^1$, $R^2$ and Y denote the same as defined below, n and p denote an integer of 1 or 2, which is characterized by adding a carboxylic acid of formula (2);

$$R^1COOH \qquad (2)$$

wherein $R^1$ denotes a hydrogen atom, an optionally substituted alkyl group or the like, an organic base to a solution of a carboxylic acid activating agent of formula (3);

$$(R^2)_pY(O)_nX \qquad (3)$$

wherein $R^2$ denotes an optionally substituted aliphatic hydrocarbyl group or the like, Y denotes a carbon atom, a phosphorus atom, or a sulfur atom, and X denotes a chlorine atom or the like.

16 Claims, No Drawings

PRODUCTION OF MIXED ACID ANHYDRIDE AND AMIDE COMPOUND

FIELD OF THE INVENTION

The present invention relates to a selective production method of a mixed acid anhydride and a production method of an amide compound, which methods are useful in the production of pharmaceuticals and intermediates thereof.

DESCRIPTION OF RELATED ART

A mixed acid anhydride of a carboxylic acid derivative has been known as an intermediate for producing an amide compound. Said anhydride has been typically produced, for example, in a small scale production by quickly adding a carboxylic add activating agent to a mixed solution of a carboxylic acid such as an amino acid having a protected amino group and an organic base, and immediately thereafter, within a few minutes, reacted with amines to produce amides due to its instability to a longer reaction time (J. Amer. Chem. Soc., 89, 5012 (1967), and Org. Reaction, 12, 157 (1962)).

SUMMARY OF THE INVENTION

According to the present invention, a mixed acid anhydride can be selectively produced, and an amide compound can be produced in a good chemical or optical yield not only in a laboratory scale but also in an industrial scale of production where a longer reaction time is required.

The present invention provides a method for producing a mixed acid anhydride of formula (1):

$$R^1C(O)OY(O)_n(R^2)_p \quad (1)$$

wherein $R^1$, $R^2$, Y, n and p denote the same as defined below, which comprises adding a carboxylic acid of formula (2);

$$R^1COOH \quad (2)$$

wherein $R^1$ denotes
a hydrogen atom,
an optionally substituted saturated or unsaturated hydrocarbyl group, or
an optionally substituted hetero ring, and
an organic base to a solution of a carboxylic acid activating agent of formula (3);

$$(R^2)_pY(O)_nX \quad (3)$$

wherein $R^2$ denotes
an optionally substituted alkyl group (e.g., C1–C6 chain, branched or cyclic alkyl group, which may be substituted with a halogen atom),
an optionally substituted aryl group (e.g., a phenyl which may be substituted with a halogen or C1–C3 alkyl group),
an optionally substituted chain or cyclic alkoxy group (e.g., C1–C6 chain or cyclic alkoxy group), or
an optionally substituted aryloxy group (e.g., a phenoxy group which may be substituted with a halogen or C1–C3 alkyl group), Y denotes
a carbon atom, a phosphorus atom, or a sulfur atom, X denotes
a fluorine atom, a chlorine atom, a bromine atom, an iodine atom, a cyano group or a group of formula:

$$(R^2)_pY(O)_nO—,$$

wherein
$R^2$ is the same as defined above,
n and p are an integer of 1 or 2; and
when Y is a carbon atom, n=1 and p=1,
when Y is a phosphorous atom, n=1 and p=2, and
when Y is sulfur atom, n=2 and p=1 and $R^2$ denotes an optionally substituted alkyl or aryl group; and
a method for producing an amide compound of formula (4);

$$R^1-\overset{O}{\underset{\|}{C}}-NR^3R^4 \quad (4)$$

wherein
$R^1$ denotes the same group as described above,
$R^3$ and $R^4$ independently denote
a hydrogen atom,
an optionally substituted saturated or unsaturated hydrocarbyl group,
an optionally substituted hetero ring,
a protective group for an amino group, or
$R^3$ represents a group of formula: —$OR^{30}$, or —$NR^{30}R^{31}$, wherein
$R^{30}$ represents an optionally substituted alkyl group, or an optionally substituted aryl group and $R^{31}$ represents a hydrogen atom or an optionally substituted aryl group, and
$R^3$ and $R^4$ may be bonded to form a ring, which comprises reacting the mixed acid anhydride of formula (3) obtained as above, with an amine of formula (5);

$$NHR^3R^4 \quad (5)$$

wherein $R^3$ and $R^4$ independently denote the same group as described above.

DETAILED DESCRIPTION OF THE INVENTION

Hereinafter, the present invention will be described in detail.

First a description will be made to $R^1$.

In the optionally substituted saturated or unsaturated hydrocarbyl group represented by $R^1$ and other groups, the saturated or unsaturated hydrocarbyl group means, unless otherwise specified hereinafter, a straight, branched or cyclic alkyl group (e.g., C1–C18 alkyl group),
an alkenyl or cycloalkenyl group (e.g., C2–C5 alkenyl or C5–C6 cycloalkenyl),
an alkynyl group (e.g., C3–C4 alkynyl),
an aryl group, which includes a phenyl, tolyl, biphenyl and naphthyl group,
an aralkyl, arylalkenyl or arylalkynyl group, which respectively means a phenyl-, biphenyl- or naphthyl-substituted alkyl (e.g, C1–C4 alkyl such as methyl, ethyl, propyl, butyl), alkenyl (e.g., C2–C4 alkenyl such as vinyl, propenyl, methally), or alkynyl (e.g, C3–C4 alkylnyl such as propynyl, butynyl) group.

The hetero ring means a pyridyl group, a 1,3-oxazole group, a 1,3-thiazole group, a furyl group, a tetrahydrofuryl group, a thienyl group, an imidazole or alkyleneimine group (e.g., C2–C11) of which nitrogen atoms are protected by a protecting group, or the like hereinafter.

The straight, branched or cyclic alkyl group, the alkenyl or cycloalkenyl group, the alkynyl group, the aryl group, the aralkyl, arylalkenyl or arylalkynyl group and the hetero ring may be each substituted with (a) a hydroxy group or a halogen atom, or
(b) an amino group of formula: $R^{11}R^{12}N$— and optionally further with
  at least one group selected from
  a carbamoyl group, a methylmercapto group,
  a 4-pyrimidinone-3-yl group,
  an alkyl(C1–C3)dithio group, of which alkyl is substituted with an amino and carboxyl groups,
  a mercapto, guanidyl, carboxyl, hydroxy or imidazolyl group, wherein $R^{11}$ represents a hydrogen atom or an amino-protecting group, $R^{12}$ represents an amino-protecting group, or a group of formula: $R^{13}$—CO, wherein $R^{13}$ represents a saturated or unsaturated hydrocarbyl group or a hetero ring, as defined above, which may be substituted with
(c) a hydroxy group, or a halogen atom, or
(d) a group of formula: $R^{14}R^{15}N$— and optionally further with at least one group selected from
  a carbamoyl group, a methylmercapto group,
  an alkyl(C1–C3)dithio group, of which alkyl is substituted with an amino and carboxyl groups,
  an amino, mercapto, guanidyl, carboxyl, hydroxy, imidazolyl group, wherein $R^{14}$ is an amino-protecting group, and $R^{15}$ represents a hydrogen atom, a saturated or unsaturated hydrocarbyl group, a hetero ring or an amino-protecting group,
  provided that said amino, mercapto, guanidyl, carboxyl, hydroxy and imidazolyl groups which may present in $R^1$, $R^2$, $R^3$ and substituent groups contained therein are in a protected form.

First preferred group for $R^1$ is an alkyl (e.g, C1–C5) group substituted with (b) an amino group of formula: $R^{11}R^{12}N$— and optionally further with
  at least one group selected from
  a carbamoyl group, a methylmercapto group,
  a 4-pyrimidinone-3-yl group,
  an alkyl(C1–C3)dithio group, of which alkyl is substituted with an amino and carboxyl groups,
  a mercapto, guanidyl, carboxyl, hydroxy or imidazolyl group, wherein $R^{11}$ represents a hydrogen atom or an amino-protecting group, $R^{12}$ represents an amino-protecting group, or a group of formula: $R^{13}$—CO, wherein $R^{13}$ represents a saturated or unsaturated hydrocarbyl group or the hetero ring, as defined above, which may be substituted with
(c) a hydroxy group, or a halogen atom, or
(d) a group of formula: $R^{14}R^{15}N$— and optionally further with at least one group selected from
  a carbamoyl group, a methylmercapto group,
  an alkyl(C1–C3)dithio group, of which alkyl is substituted with an amino and carboxyl groups,
  an amino, mercapto, guanidyl, carboxyl, hydroxy, imidazolyl group, wherein $R^{14}$ is an amino-protecting group, and $R^{15}$ represents a hydrogen atom or an amino-protecting group,
  provided that said amino, mercapto, guanidyl, carboxyl, hydroxy and imidazolyl groups are in a protected form.

Specific examples of the optionally substituted (C1–C18) alkyl group include a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, an n-dodecyl group, a n-tridecyl group, a n-tetradecyl group, a n-pentadecyl group, an n-hexadecyl group, an n-heptadecyl group, an octadecyl group, an isopropyl group, an isobutyl group, a 3-methylbutyl group, a 4-methylpentyl group, a 5-methylhexyl group, a 6-methylheptyl group, a 7-methyloctyl group, a 8-methylnonyl group, a see-butyl group, a 2-methylbutyl group, a 2-methylpentyl group, a 2-methylhexyl group, a 2-methylheptyl group, a 2-methyloctyl group, a 2-methylnonyl group, a t-butyl group, a cyclohexyl group, a 1-hydroxy-n-butyl group, a 2-hydroxy-1-cyclohexyl group, and the like, wherein the hydroxy groups are in a protected form.

Specific examples of the optionally substituted aryl or aralkyl group include an α-phenethyl group, a 1-hydroxy-1-phenylmethyl group, or the like, a phenyl group, a 4-methylphenyl group,
a 4-phenylphenyl group, a 4-hydroxyphenyl group, or the like, wherein the hydroxy groups are in a protected form.

In addition, $R^1$ group includes the following sub-group of formula:

$$R^{11}R^{12}N—A— \quad (6)$$

wherein $R^{11}$ and $R^{12}$ are the same as defined above, and "A" represents alkylene groups such as an ethylene group, a cyclohexylene group or the like,
alkenylene groups such as propenylene, cyclohexenylene or the like,
alkynylene groups such as propynylene or the like,
arylene groups such as a phenylene group or the like,
an aralkylene groups such as phenylmethylene group or the like,
arylalkenylene groups such as phenylpropynylene or the like,
arylalkynylene group such as phenypropenylene or the like, and
hetero rings such as an oxazole ring, a thiazole ring, an imidazole ring or the like.

Specific examples of the amino acids, which contain the structure of formula (6) include 3-aminopropionic acid, 3-aminobutyric acid, 3-amino-3-phenylbutyric acid, 4-aminobutyric acid, 3-aminovaleric acid, 4-aminovaleric acid, 5-aminovaleric acid, piperidine-3-carboxylic acid, piperidine-4-carboxylic acid, 2-aminocyclohexanecarboxylic acid, 3-aminocyclohexanecarboxylic acid, 4-aminocyclohexanecarboxylic acid, 3-aminoacrylic acid, 3-aminomethacrylic acid, 3-aminocyclohexene-1-carboxylic acid, 4-aminocyclohexene-1-carboxlic acid, o-aminobenzoic acid, m-aminobenzoic acid, p-aminobenzoic acid, o-aminophenylacetic acid, m-aminophenylacetic acid, p-aminophenylacetic acid, o-aminocinnamic acid, m-aminocinnamic acid, p-aminocinnamic acid, 3-(2-aminophenyl)-2-propionic acid, 3-(3-aminophenyl)-2- propionic acid, 3-(4-aminophenyl)-2-propionic acid, 2-amino-4-oxazolecarboxylic acid, 2-amino-4-thiazolecarboxylic acid, 2-amino-4-diazolecarboxylic acid or the like.

The acid derivatives represented by formula (2) include following α-amino acid derivatives of formula (7);

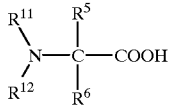

(7)

wherein $R^5$ and $R^6$ represent a hydrogen atom or a saturated or unsaturated hydrocarbyl group or a hetero ring, both of which may be each substituted with (a) a hydroxy group or a halogen atom, or (b) at least one group selected from
a carbamoyl group, a methylmercapto group,
an alkyl(C1–C3)dithio group, of which alkyl is substituted with a protected amino and carboxyl groups, and
a protected amino, mercapto, guanidyl, carboxyl, hydroxy or imidazolyl group, $R^{11}$ is a hydrogen atom or an amino-protecting group, $R^{12}$ represents an amino-protecting group or a group of formula: $R^{13}CO-$, wherein $R^{13}$ represents a saturated or unsaturated hydrocarbyl group or the hetero ring, which may be substituted with (c) a hydroxy or a halogen atom, or (d) a group of formula: $R^{14}R^{15}N-$ and optionally further with at least one group selected from
a carbamoyl group, a methylmercapto group,
alkyl(C1–C3)dithio group, of which alkyl is substituted with a protected amino and carboxyl groups,
an amino, mercapto, guanidyl, carboxyl, hydroxy, or imidazolyl group, wherein $R^{14}$ is an amino-protecting group, $R^{15}$ represents a hydrogen atom or an amino-protecting group, and $R^{11}$ and $R^{12}$, and $R^{14}$ and $R^{15}$ may independently form an alkyleneimie group such as aziridine, azetidine, or a 4-pyrimidinone-3-yl group or the like, provided that said amino, mercapto, guanidyl, carboxyl, hydroxy and imidazolyl group are in a protected form.

Specific examples of the α-amino acids, which are encompassed by the formula (7) include
alanine, arginine, asparagine, aspartic acid, cysteine, cystine, glutamic acid, glutamine, histidine, hydroxylysine, isoleucine, leucine, lysine, methionine, phenylalanine, proline, serine, threonine, tryptophane, tyrosine, valine, 1-naphthylalanine, 2-naphthylalanine, pipecoline, ornithine, 2,2-dimethylglycine, 2-pyridylalanine, 3-pyridylalanine, 4-pyridylalanine, 2-chlorophenylalanine, 3-chlorophenylalanine, 4-chlorophenylalanine, 4-pyrimidinone-3-acetic acid or the like, of which functional groups other than carboxyl groups are protected.

Examples of the alkyleneimine compounds, which is encompassed by the formula (7) above, include a cyclic α-amino acid derivative of formula (8):

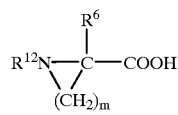

(8)

wherein $R^{12}$ and $R^6$ independently denote the same as described above, and m denotes an integer from 1 to 10.

Specific examples of the compounds defined by the general formula (8) include
aziridinecarboxlic acid, azetidinecarboxyic acid, proline, hydroxyproline, pipecolic acid, 2-carboxyhexamethyleneimine, 2-carboxyheptamethyleneimine, 2-carboxyoctamethyleneimine, 2-carboxynonamethyleneimine, 2-carboxydecamethyleneinmine, 2-carboxyundecamethyleneimine, 2-carboxydodecamethyleneimine, 2-carboxytridecamethyleneimine, 2-carboxytetradecamethyleneimine, 2-carboxypentadecamethyleneimine, 2-carboxyhexadecamethyleneimine, 2-carboxyheptadecamethyleneimine, 2-carboxyoctadecamethyleneimine, 2-carboxynonadecamethyleneimine, 2-carboxyeicosamethyleneimine, 2-carboxyheneicosamethyleneimine or the like, of which nitrogen atom is protected.

Specific examples of the dipeptide, which is encompassed by the formula (7) and can be derived from the specified α-amino acids above include
alanyl-azetidinecarboxylic acid, alginyl-azetidinecarboxylic acid, asparaginyl-azetidinecarboxylic acid, aspartyl-azetidinecarboxylic acid, cysteinyl-azetidinecarboxylic acid, cystyl-azetidinecarboxylic acid, glutamyl-azetidinecarboxylic acid, glycyl-azetidinecarboxylic acid, histidyl-azetidinecarboxylic acid, hydroxylysyl-azetidinecarboxylic acid, isoleucyl-azetidinecarboxylic acid, leucyl-azetidinecarboxylic acid, lysyl-azetidinecarboxylic acid, methionyl-azetidinecarboxylic acid, phenylalanyl-azetidinecarboxylic acid, prolyl-azetidinecarboxylic acid, seryl-azetidinecarboxylic acid, threonyl-azetidinecarboxylic acid, tryptophyl-azetidinecarboxylic acid, tyrosyl-azetidinecarboxylic acid, valyl-azetidinecarboxylic acid, naphthylalanyl-azetidinecarboxylic acid, pipecolyl-azetidinecarboxylic acid, ornithyl-azetidinecarboxylic acid, 2,2-dimethylglycyl-azetidinecarboxylic acid, 4-pyrimidinon-3-acetyl-azetidinecarboxylic acid, azetidyl-azetidinecarboxylic acid or the like, of which functional groups other than α-carboxyl group are protected.

Specific examples of the protecting groups in the present specification, for example, those represented by $R^{11}$, $R^{12}$, $R^{13}$, $R^{14}$ and $R^{15}$ which protect the functional groups such as a hydroxy, mercapto, amino, carboxyl, or guanidyl group in $R^1$, include carbamate type protective groups such as
a methyloxycarbonyl group, an ethyloxycarbonyl group, an isobutyloxycarbonyl group, a t-butyloxycarbonyl group, a t-amyloxycarbonyl group, a 2,2,2-trichloroethyloxycarbonyl group, a 2-trimethyl- silylethyloxycarbonyl group, a phenylethyloxycarbonyl group, a 1-(1-adamantyl)-1-methylethyloxycarbonyl group, a 1,1-dimethyl-2-haloethyloxycarbonyl group, a 1,1-dimethyl-2,2-dibromoethyloxycarbonyl group, a 1,1-dimethyl-2,2,2-trichloroethyloxycarbonyl group, a methyl-1-(4-biphenylylethyloxycarbonyl group, a 1-(3, 5-di-tert-butylphenyl)-1-methylethyloxycarbonyl group, a 2-(2'-pyridyl)ethyloxycarbonyl group, a 2-(4'-pyridyl)ethyloxycarbonyl group, a 2-(N,N-dicyclohexylcarboxamido)ethyloxycarbonyl group, a 1-adamantyloxycarbonyl group, a vinyloxycarbonyl group, an allyloxycarbonyl group, a 1-isopropylallyloxycarbonyl group, a cinnamyloxycarbonyl group, a 4-nitrocinnamyloxycarbonyl group, an 8-quinolyloxycarbonyl group, an N-hydroxypiperidinylcarbonyl group, an alkyldithiocarbonyl group, a benzyloxycarbonyl group, a p-methoxybenzyloxycarbonyl group, a p-nitrobenzyloxycarbonyl group, a p-bromobenzyloxycarbonyl group, a p-chlorobenzyloxycarbonyl group, a 2,4-dichlorobenzyloxycarbonyl group, a 4-methylsulfinylbenzyloxycarbonyl group, a 9-anthrylmethyloxycarbonyl group, a dipheylmethyloxycarbonyl group, a 9-fluorenylmethyloxycarbonyl group, a 9-(2,7-dibromo)fluorenylmethyloxycarbonyl group, a 2,7-di-t-butyl[9-(10,10-dioxo-thioxantyl) methyloxycarbonyl group, a 4-methoxyphenacyloxycarbonyl group, a 2-methylthioethyloxycarbonyl group, a 2-methylsulfonylethyloxycarbonyl group, a 2-(p-toluenesulfonyl)ethyloxycarbonyl group, a [2-(1,3-dithianyl)]methyloxycarbonyl group, a 4-methylthiophenyloxycarbonyl group, a 2,4-dimethylthiophenyloxycarbonyl group, a 2-phosphonioethyloxycarbonyl group, a 2-triphenylphosphonioisopropyloxycarbonyl group, a 1,1-dimethyl-2-cyanoethyloxycarbonyl group, a m-chloro-p-acyloxybenzyloxycarbonyl group, a p-(dihydroxyboryl)benzyloxycarbonyl group, a 5-benzoisooxazolylmethyloxycarbonyl group, a 2-(trifluoromethyl)-6-chromonylmethyloxycarbonyl group, a phenyloxycarbonyl group, m-nitrophenyloxycarbonyl group, a 3,5-dimethoxybenzyloxycarbonyl group, a o-nitrobenzyloxycarbonyl group, a 3,4-dimethoxy-6-nitrobenzyloxycarbonyl group, a phenyl(o-nitrophenyl)methyloxycarbonyl group or the like, amide type protective groups such as a formyl group, an acetyl group, a chloroacetyl group, a trichloroacetyl group, a trifluoroacetyl group, a phenylacetyl group, a benzoyl group or the like, an alkyl type protective group such as benzyl group, N-di(4-methoxyphenyl) methyl group, a N-5-dibenzosuberyl group, a N-triphenylmethyl group, a (4-methoxyphenyl) diphenylmethyl group, a N-9-phenylfluorenyl group, an allyl group, a N-[2-(trimethylsilyl)ethoxy]methyl group, a N-3-acetoxypropyl group or the like.

Said α-amino acids are commercially available or can be produced by a known methods and the protective groups can be optionally introduced and deprotected as discussed in detail by T. Greene in Protective Groups in Organic Synthesis, John Wiley & Sons, New York, 1981.

The protecting group of an amino group includes, for example, Z, Boc, tertiary-amyloxycarbonyl, isobornyloxycarbonyl, 4-methoxybenzyloxycarbonyl, Cl-Z, Br-Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned as well as 2-adamantyl, 4-nitrobenzyl, 4-methoxybenzyl, 4-chlorobenzyl, phenacyl, benzyloxycarbonylhydrazido, tertiary-butoxycarbonylhydrazido, tritylhydrazido and the like. Preferred is Boc.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl.

The protective group for the phenolic hydroxyl group of tyrosine includes 2-nitrobenzyl, Br—Z, tertiary-butyl or the like.

The protecting group of imidazole for histidine or guanidyl group for arginin includes Tos, 4-methoxy-2,3,6-trimethylbenzenesulfonyl, DNP, benzyloxymethyl, Bum, Boc, Trt, and Fmoc.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of 20° C. to 40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

For example, removal of BOC protecting groups can be carried out using a strong acid such as trifluoroacetic acid or hydrochloric acid with or without the presence of a co-solvent such as dichloromethane or methanol at a temperature of about −30° C. to 70° C., preferably about −5° C. to about 35° C.

The method for protecting functional groups which should not take part in the reaction of the starting material, the protective groups that can be used, the method of removing the protective groups, and the method of activating the functional groups that are to take part in the reaction can all be selected from among the known groups and methods.

A description will be made to $R^2$ as below.

Examples of the C1–C6 chain, branched or cyclic alkyl group, which may be substituted with a halogen atom include methyl, ethyl, n-propyl, n-butyl, isopropyl, sec-butyl, isobutyl, isoamyl, cyclopentyl, cyclohexyl, 3-pentyl, 2,2-dimethylpropyl, trifluoromethyl or the like Examples of the phenyl which may be substituted with a halogen or C1–C3 alkyl group include phenyl, tolyl, mesityl, p-chlorophenyl and the like.

Examples of the C1–C6 chain or cyclic alkoxy group include methoxy, ethoxy, n-propoxy, n-butoxy, isopropoxy, sec-butoxy, isobutoxy, isoamyloxy, cyclopentyloxy, cyclohexyloxy, 3-pentyloxy, 2,2-dimethylpropyloxy, and the like.

Examples of the phenoxy group which may be substituted with a halogen or C1–C3 alkyl group include a phenoxy, tolyloxy, mesityloxy and the like.

Examples of the carboxylic acid activating agent defined by the formula (3) for producing a mixed acid anhydride from a carboxylic acid and a carboxylic acid activating agent in the presence of an organic base include carbon-type acid chlorides such as methyl chlorocarbonate, ethyl chlorocarbonate, n-propyl chlorocarbonate, n-butyl chlorocarbonate, isopropyl chlorocarbonate, sec-butyl chlorocarbonate, isobutyl chlorocarbonate, isoamyl chlorocarbonate, cyclopentyl chlorocarbonate, cyclohexyl chlorocarbonate, valeryl chloride, isovaleryl chloride, diethylacethyl chloride, pivaloyl chloride or the like, phosphorus-containing acid chlorides such as diethylphosphoryl chloride, diphenylphosphoryl chloride, diphenylphosphine chloride or the like, sulfur-containing acid chlorides such as methanesulfonyl chloride, ethanesulfonyl chloride, trifluoromethanesulfonyl chloride, p-toluenesulfonyl chloride, benzenesulfonyl chloride, mesitylenesulfonyl chloride or the like, carbon-containing type acid anhydrides such as acetic acid anhydride, trifluoroacetic acid anhydride or the like, phosphorus-containing type acid anhydrides such as, ethylmethylphosphinic acid anhydride, a cyclic trimer of n-propylphosphonic acid anhydride or the like, and sulfur-containing type acid anhydrides such as trifluoromethanesulfonic acid anhydride. Further, bromides, fluorides, and iodides are also included in place of the chlorides.

The amount of the carboxylic acid activating agent is usually 0.5 to 5 moles, preferably 0.9 to 1.1 moles, more preferably 0.95 to 1.05 mol per mol of the carboxylic acid defined by the formula (1).

In the production of the mixed acid anhydride, examples of the organic base to be used include organic tertiary base such as trimethylamine, ethyldimethylamine, dimethyl-n-propylamine, dimethylisopropylamine, cyclohexyldimethylamine, benzyldimethylamine, dimethylphenylamine, diethylmethylamine, methyl-di-n-propylamine, methyldiisopropylamine, triethylamine, ethyldiisopropylamine, tri-n-propylamine, tri-n-butylamine, tri-n-pentylamine, tri-n-hexylamine, tri-n-heptylamine, tri-n-octylamine, quinuclidine, N-methylmorpholine, N-ethylmorpholine, N,N'-dimethylpiperazine, N-methylpyrrolidine, N-methylpiperidine. pyridine, quinoline, isoquinoline, N-methylimidazole or the like. Preferred is N-methylmorpholine.

The amount of the organic base to be used is usually 0.5 to 50 moles, preferably 0.9 to 2 moles, more preferably 0.95 to 1.05 moles per mol of the carboxylic acid defined by the formula (1).

In the present invention, the carboxylic acid defined by the formula (1) may be added as a solution containing the organic base to the carboxylic acid activating agent, alternatively, the carboxylic acid solution and the organic base may be added separately and simultaneously.

Examples of a reaction solvent that can be usually used for producing the mixed acid anhydride include esters such as methyl acetate, ethyl acetate, n-propyl acetate, isopropyl acetate, n-butyl acetate, isobutyl acetate, sec-butyl acetate, n-pentyl acetate, isopentyl acetate, sec-pentyl acetate, n-hexyl acetate, isohexyl acetate, sec-hexyl acetate, methyl cellosolve acetate, ethyl propionate, ethyl n-valerate or the like, ethers such as tetrahydrofuran, dioxane, 1,3-dioxolan, dimethoxymethane, dimethoxyethane, diethyl ether, tert-butyl methyl ether or the like, aprotic polar solvents such as acetonitrile, N,N'-dimethylformamide, N,N'-dimethylacetamide, N-methylpyrrolidone, pyridine or the like, halogenated hydrocarbons such as chlorobenzene, dichloromethane, chloroform, 1,2-dichloroethane or the like, and hydrocarbons such as toluene, xylene, benzene, hexane, heptane or the like.

The reaction temperature for producing the mixed acid anhydride is usually within a range of about −78 to about 30° C. and preferably about −20 to about 10° C., The mixed acid anhydride thus produced may be maintained at the reaction temperature for 30 minutes and then reacted with an amine.

In the amine compound of formula (4), the saturated or unsaturated hydrocarbyl group in the optionally substituted saturated or unsaturated hydrocarbyl group represented by $R^3$ or $R^4$ include a straight, branched or cyclic alkyl group (e.g., C1–C18 alkyl group), an alkenyl or cycloalkenyl group (e.g., C2–C5 alkenyl or C5–C6 cycloalkenyl), an alkynyl group (e.g., C3–C4 alkynyl), an aryl group, which include a phenyl, tolyl, biphenyl and naphthyl group, an aralkyl, arylalkenyl or arylalkynyl group, which respectively means a phenyl-, biphenyl- or naphthyl-substituted alkyl (e.g, C1–C4 alkyl such as methyl, ethyl, propyl, butyl), alkenyl (e.g., C2–C4 alkenyl such as vinyl, propenyl, methally), or alkynyl (e.g, C3–C4 alkylnyl such as propynyl, butynyl) group.

The hetero ring means a pyridyl group, a 1,3-oxazole group, a 1,3-thiazole group, a furyl group, a tetrahydrofuryl group, a thienyl group, an imidazole or an alkyleneimine group (e.g., C2–C11) of which nitrogen atoms are protected by a protecting group, or the like.

Said saturated or unsaturated hydrocarbyl group and the hetero ring may be substituted with at least one group selected from a halogen, nitro, alkoxy(e.g., C1–C3 alkoxy), alkyl (e.g, C–C3 alkyl), a hydroxy group, a cyano group, or a (2-alkoxyiminoacetate)-2-yl group, a carbamoyl group, a methylmercapto group, an alkyl(C1–C3)dithio group, of which alkyl is substituted with a protected amino and carboxyl groups, an amino, mercapto, guanidyl, carboxyl, hydroxy, or imidazolyl group, a group of formula: $C(O)-R^8$, wherein $R^8$ is an alkoxy group or a group of formula: $NHR^{80}$ wherein $R^8$ and $R^{80}$ represent a saturated or unsaturated hydrocarbyl group or the hetero ring, as defined above, both of which may be substituted with a group of formula: $C(O)R^{81}$ or a hydroxy group and optionally further with at least one group selected from a carbamoyl group, a methylmercapto group, alkyl(C1–C3)dithio group, of which alkyl is substituted with an amino and carboxyl groups, an amino, mercapto, guanidyl, carboxyl, hydroxy, or imidazolyl group, wherein $R^{81}$ is an alkoxy group or a group of formula: $NHR^{82}$ wherein $R^{81}$ and $R^{82}$ represent a saturated or unsaturated hydrocarbyl group or the hetero ring as defined above, provided that said amino, mercapto, guanidyl, carboxyl, hydroxy, and imidazolyl groups above are in a protected form.

Specific examples of $R^{30}$ an $R^{31}$ include a methyl, an ethyl group, or a phenyl group.

Specific examples of the amines to be used include ammonia, a mono- or di-alkyl(C1–C12)amine such as methylamine, ethylamine, n-propylamine, n-butylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isoöetylamine, isononylamine, isodecylamine, isoundecylamine, isododecylamine, isopropylamine, sec-butylamine, sec-pentylamine, sec-hexylamine, sec-heptylamine, sec-octylamine, sec-nonylamine, sec-decylamine, sec-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine or the like, an arylalkylamine, of which aralkyl group (e.g., benzyl group, or phenethyl) may be substituted with a cyano, halogen, alkoxy, alkyl) such as benzylamine, o-cyanobenzylamine, m-cyanobenzylamine, o-halobenzylamine, m-halobenzylamine, p-halobenzylamine, o-methoxybenzylamine, m-methoxybenzylamine, p-methoxybenzylamine, o-nitrobenzylamine, m-nitrobenzylamine, p-nitrobenzylamine, o-alkylbenzylamine, m-alkylbenzylamine, p-alkylbenzylamine, phenetylamine, N-alkylbenzylamine or the like, an arylamine, of which aryl group (e.g., phenyl or naphthyl) may be substituted with a cyano group, halogen atom (fluorine, chlorine, bromine, or iodine), nitro, alkyl, alkoxy, or aryl), such as phenylamine, o-cyanophenylamine, m-cyanophenylamine, p-cyanophenylamine, o-halophenylamine, m-halophenylamine, p-halophenylamine, o-methoxyphenylamine, m-methoxyphenylamine, p-methoxyphenylamine, o-nitrophenylamine, m-nitrophenylamine, p-nitrophenylamine, o-alkylphenylamine, m-alkylphenylamine, p-alkylphenylamine, N-alkylphenylamine, N-arylphenylanine or the like, amino acid esters such as azetidine carboxylic acid ester, alanine ester, arginine ester, asparagine ester, aspartic acid ester, cysteine ester, cystine ester, glutamic acid ester, glutamine ester, glycine ester, histidine ester, hydroxylysine ester, hydroxyproline ester, isoleucine ester, leucine ester, lysine ester, methionine ester, phenylalanine ester, proline ester, serine ester, threonine ester, tryptophane ester, tyrosine ester, valine ester, naphthylalanine ester, pipecolic acid ester, ornithine ester, or the like, peptides such as alanyl-azetidinecarboxylate, arginyl-azetidinecarboxylate, asparaginyl-azetidinecarboxylate, aspartyl-azetidinecarboxylate, cysteinyl-azetidinecarboxylate, cystyl-azetidinecarboxylate, glutamyl-azetidinecarboxylate, glycyl-azetidinecarboxylate, histidyl-azetidinecarboxylate, hydroxylysyl-azetidinecarboxylate, isoleucyl-azetidinecarboxylate, leucyl-azetidinecarboxylate, lysyl-azetidinecarboxylate, methionyl-azetidinecarboxylate, phenylalanyl-azetidinecarboxylate, proryl-azetidinecarboxylate, seryl-azetidinecarboxylate, threonyl-azetidinecarboxylate, tryptophyl-azetidinecarboxylate, tyrosyl-azetidinecarboxylate, valyl-azetidinecarboxylate, naphthylalanyl-azetidinecarboxylate, pipecolyl-azetidinecarboxylate, ornithyl-azetidinecarboxylate, 2,2-dimethylglycyl-azetidinecarboxylate, 4-pyrimidinon-3-acetyl-azetidinecarboxylate, azetidyl-azetidinecarboxylate or the like, 2-aminooxazoles, 2-aminoimidazoles, 2-aminothiazoles, hydroxylamines such as N,O-dimethylhydroxylamines, and hydrazines such as 1-methyl-1-phenylhyrazine.

The amines may be hydrochlorides, methanesulfonic acid salts, p-toluenesulfonic acid salts, benzenesulfonic acid salts or the like. In such cases, the base in an amount of equal to or more than the equivalent to the organic amine is used to liberate it in the reaction system.

The amount of the amine to be used is usually about 0.5 to about 5 moles, preferably 0.7 to 2 moles per mol of the carboxylic acid defined by the general formula (1).

When Y is not a carbon atom and $R^2$ is not an optionally substituted alkoxy or aryloxy group, a base is usually used to neutralize an acid formed in the amidation reaction of the amine and the mixed acid anhydride of the present invention. The amount of the base is usually 1 mol per mol of the mixed acid anhydride, if necessary. Examples of the base include the tertiary organic amines as exemplified above.

As a reaction solvent to be used for the amidation reaction, the foregoing solvents exemplified for those to be used for the mixed acid anhydride production can be used. The amount is not specifically limited.

The reaction temperature of the amidation reaction is usually within a range of −78 to 50° C. and preferably −20 to 30° C.

After completion of the reaction, the obtained reaction mixture is successively washed with an aqueous acid, water, alkaline and water and an amide compound as defined by the general formula (5) can be obtained.

In the production of a mixed acid anhydride from the carboxylic acid and the carboxylic acid activating agent in the presence of an organic base, if the carboxylic acid activating agent is dropwise added to a solution containing the carboxylic acid and the organic base according to a conventional reaction method, as shown in the comparative examples, acid anhydrides are produced as by-products and the selectivity in the production of the mixed acid anhydride is rather low.

On the other hand, according to the reaction method of the present invention, that is, the carboxylic acid and the organic base are dropwise added to a solution containing the carboxylic acid activating agent, the selectivity of production of the mixed acid anhydride is significantly improved.

Thus, an amide compound can be produced in a good yield using the mixed acid anhydride produced in the present invention in a reaction with an amine.

The present invention is effective in the case where the yield is insufficient by a conventional method. Further, the present invention is particularly advantageous in terms of industrial production since a desired product can be obtained in a good yield for an amidation reaction by conventional method where the yield is decreased owing to long addition time.

EXAMPLES

Hereinafter, the present invention will more particularly be described along with examples, but it is not to be construed to limit the present invention thereto.

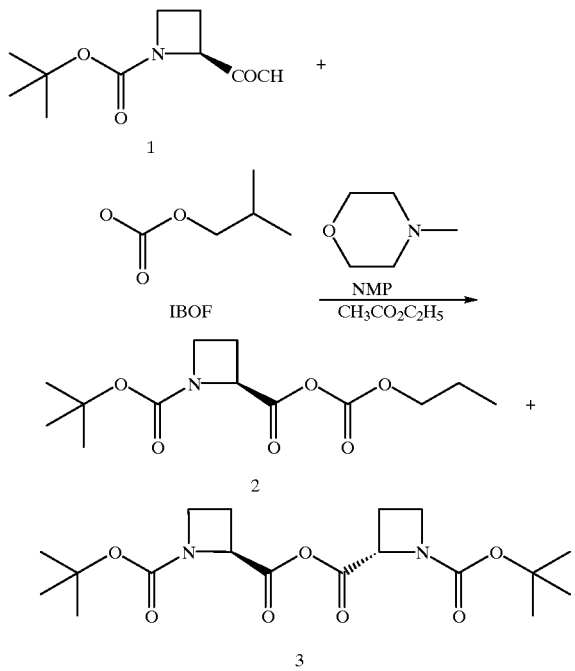

Example 1

A substrate solution was produced by adding N-methylmorpholine (5.03 g, 0.0497 mole) to Boc-L-azetidinecarboxylic acid 1 (10.00 g, 0.0497 mol) and ethyl acetate (26 g) at a room temperature and dissolved under stirring. To a well-dried reaction container equipped with a stirring apparatus, a thermometer, and a addition funnel, purged with nitrogen, are added isobutyl chlorocarbonate (6.79 g, 0.0497 mol) and ethyl acetate (26 g) and cooled to −10° C. under stirring. The substrate solution prepared above was dropwise added in 1.5 hours at −1.5±2° C. The resultant solution was kept at the temperature for 30 minutes and a portion (about 100 mg) of the produced slurry was isolated and mixed with tetrahydrofuran (5 mL) for high performance liquid chromatography and thoroughly stirred and filtered through a membrane filter. The filtrate was immediately analyzed by high-performance liquid chromatography (by Solovaks CN column 4.6φ×250 mm; hexane/THF (0.1% trifluoroacetic acid); 85/15; UV 210 nm), and when the integrated surface percentage ratio 2/3 of the mixed acid anhydride 2 (retention time 5.8 minutes) and an acid anhydride 3 (retention time 10.6 minutes) was calculated and found 97.5/2.5 (excluding blank). No substrate 1 (retention time 7.8 minutes) was detected.

Example 2

The same procedure was carried out in a similar manner as in Example 1 except that the loading amount of N-methylmorpholine was 5.13 g (0.0507 mole) and addition of the substrate solution was carried out in 0.75 hours and the ratio for 2/3 was 96.6/3.4. No substrate 1 was detected.

Example 3

The same procedure was carried out in a similar manner as in Example 1 except that the amount of N-methylmorpholine was 5.33 g (0.0527 mole) and addition of the substrate solution was carried out in 0.75 hours and the ratio for 2/3 was 90.3/9.7. No substrate 1 was detected.

Example 4

The same procedure was carried out in a similar manner as in Example 1 except that the amount of N-methylmorpholine was 4.93 g (0.0487 mole) and addition of the substrate solution was carried out in 0.75 hours and the ratio for 2/3 was 96.5/2.6. The balance 0.9% was of the remaining substrate 1.

Example 5

The same procedure was carried out in a similar manner as in Example 1 except that the amount of N-methylmorpholine was 5.53 g (0.0547 mole) and addition of the substrate solution was carried out in 0.75 hours and the temperature was kept at 5±2° C. and the ratio for 2/3 was found 84.7/13.4. The balance 1.9% was of isobutyl ester of the substrate and no substrate 1 was detected.

Example 6

The same procedure was carried out in a similar manner as in Example 1 except that the amount of N-methylmorpholine was 5.53 g (0.0547 mole) and addition of the substrate solution was carried out in 0.75 hours and the ratio for 2/3 was found 85.4/14.6. No substrate 1 was detected.

Example 7

The same procedure was carried out in a similar manner as in Example 1 except that the loading amount of N-methylmorpholine was 5.53 g (0.0547 mole) and addition of the substrate solution was carried out in 0.75 hours and the temperature was kept at −12±2° C. and the ratio for 2/3 was 85.0/15.0. No substrate 1 was detected.

Example 8

The same procedure was carried out in a similar manner as in Example 1 except that the amount of N-methylmorpholine was 5.53 g (0.0547 mole) and the ratio for 2/3 was 84.8/15.2. No substrate 1 was detected.

Example 9

The same procedure was carried out in a similar manner as in Example 1 except that the amount of N-methylmorpholine was 5.53 g (0.0547 mole) and the addition of the substrate solution was carried out in 3 hours and the ratio for 2/3 was 84.6/15.4. No substrate 1 was detected.

Example 10

The same procedure was carried out in a similar manner as in Example 1 except that the amount of N-methylmorpholine was 5.53 g (0.0547 mole) and the addition of the substrate solution was carried out in 8 hours and the ratio for 2/3 was 79.7/19.7. No substrate 1 was detected.

Example 11

The substrate solution was produced in a same manner as in Example 1 except that the amount of N-methylmorpholine was 5.53 g (0.0547 mole). To a well-dried reaction container equipped with a stirring apparatus, a thermometer, and a dropping funnel, purged with nitrogen, were added isobutyl chlorocarbonate (6.79 g, 0.0497 mol) and the inner temperature was cooled below −10° C. under stirring. The substrate solution thus produced was dropwise added in 1.5 hours at an inner temperature of −5±2° C. The resultant solution was kept at the temperature for 30 minutes. The ratio for 2/3 was 88.5/11.5. No substrate 1 was detected.

Comparative Example 1

To a well-dried reaction container equipped with a stirring apparatus, a thermometer and a dropping funnel, purged with nitrogen, were added Boc-L-azetidinecarboxylic acid (10.00 g, 0.0497 mol), ethyl acetate (26 g) and N-methylmorpholine (5.53 g, 0.0547 mole) and dissolved under stirring and the inner temperature was cooled to −10° C. Isobutyl chlorocarbonate (6.79 g, 0.0497 mol) was dropwise added to the previously produced solution in 1.5 hours at an inner temperature of −5±2° C. The resultant solution was kept at the temperature for 30 minutes. The ratio for 2/3 was 21.3/78.7. No substrate 1 was detected.

The above-described results are shown in the following table.

(1.42 g, 0.0124 mol) was dropwise added to the resultant solution in 1.5 minutes at −25 to −20° C. inner temperature. The resultant solution was kept at −20 to −10° C. for 8 hours. Some of the produced slurry was taken out and filtered through a membrane filter and the filtered slurry was subjected to the high performance liquid chromatography analysis and found that no 1 was detected and find only a peak at 10.6 minute retention time. Further, the filtration residue was dissolved in water and subjected to reverse high performance liquid chromatography analysis for analysis of 1 and found no 1 detected. Consequently, the peak at the 10.6 minute was determined to be the substance 3.

Example 12

Synthesis of Boc-L-azetidinecarboxylic acid n-butylamide using the mixed acid anhydride mass obtained according to Example 1

A substrate solution was produced by adding N-methylmorpholine (5.03 g, 0.0497 mole) to Boc-L-azetidinecarboxylic acid 1 (10.00 g, 0.0497 mol) and ethyl acetate (26 g) at a room temperature, and stirred to dissolve. A well-dried reaction container equipped with a stirring apparatus, a thermometer, and a dropping funnel was purged with nitrogen, and isobutyl chlorocarbonate (6.79 g, 0.0497

TABLE 1

Highly selective synthesis of a mixed acid anhydride 2

| No. | Supply method | Solvent amount (WR) | MMP (MR) | Addition time (h) | Addition temperature (° C.) | 2/3 |
|---|---|---|---|---|---|---|
| Example 1 | adding the solution containing 1 to IBCF | 5.2 | 1.0 | 1.5 | −5 ± 2 | 97.5/2.5 |
| Example 2 | adding the solution containing 1 to IBCF | 5.2 | 1.02 | 0.75 | −5 ± 2 | 96.6/3.4 |
| Example 3 | adding the solution containing 1 to IBCF | 5.2 | 1.06 | 0.75 | −5 ± 2 | 90.3/9.7 |
| Example 4 | adding the solution containing 1 to IBCF | 5.2 | 0.98 | 0.75 | −5 ± 2 | 96.5/2.6 |
| Example 5 | adding the solution containing 1 to IBCF | 5.2 | 1.1 | 0.75 | 5 ± 2 | 84.7/13.4 |
| Example 6 | adding the solution containing 1 to IBCF | 5.2 | 1.1 | 0.75 | −5 ± 2 | 85.4/14.6 |
| Example 7 | adding the solution containing 1 to IBCF | 5.2 | 1.1 | 0.75 | −12 ± 2 | 85.0/15.0 |
| Example 8 | adding the solution containing 1 to IBCF | 5.2 | 1.1 | 1.5 | −5 ± 2 | 84.8/15.2 |
| Example 9 | adding the solution containing 1 to IBCF | 5.2 | 1.1 | 8 | −5 ± 2 | 84.6/15.4 |
| Example 10 | adding the solution containing 1. to IBCF | 5.2 | 1.1 | 8 | −5 ± 2 | 80.2/19.8 |
| Example 11 | adding the solution containing 1 to IBCF | 2.6 | 1.1 | 1.5 | −5 ± 2 | 88.5/11.5 |
| Comparative Example 1 | adding IBCF to the solution containing 1 | 2.6 | 1.1 | 1.5 | −5 ± 2 | 21.3/78.7 |

WR: weight ratio to 1. MR: mole ratio to 1. 2/3: LC integrated surface percentage ratio (%) excluding blank.

Reference Example 1

Determination of the Retention Time of the Acid Anhydride

A well-dried reaction container equipped with a stirring apparatus, a thermometer, and a dropping funnel was purged with nitrogen, and Boc-L-azetidinecarboxylic acid (5.00 g, 0.0248 mol), t-butyl methyl ether (40 g), and N-methylmorpholine (3.77 g, 0.0373 mole) were added at a room temperature and dissolved while being stirred and then the inner temperature was cooled to −25° C. Mesyl chloride mol) and ethyl acetate (26 g) were added to the container and cooled to an inner temperature of −10° C. under stirring. Then, the substrate solution thus produced was dropwise added thereto in 1.5 hours at an inner temperature of −5±2° C. and kept at the temperature for 30 minutes. Further, n-butylamine (3.63 g, 0.0497 mol) was dropwise added to the solution in 1 hour at −5° C. or lower and the resultant solution was kept at the temperature for 3 hours. After completion of the reaction, 1% hydrochloric acid (35 g) was dropwise added thereto at 10° C. or lower and after stirred for 30 minutes, settled and separated. The obtained organic layer was washed with 9% saline water (17 g) at 5 to 10° C., settled and separated. The obtained organic layer was washed with an aqueous 5% sodium hydrogen carbonate solution (8 g) at 15 to 30° C., settled and separated. After that, the organic layer was washed with ion-exchange water (15 g) at 25 to 35° C., settled and separated. The obtained organic layer was evaporated to obtain a solution (21.8 g) of the desired pale yellowish transparent product. The content was found 56.1% by high performance liquid chromatography analysis. The pure product obtained was 12.23 g (yield 96.0% based on "1").

Example 12–2

Desired amide compounds are obtained in a similar manner by using various kinds of amines in place of n-butylamine in Example 12 as follows: ammonia, methylamine, ethylamine, n-propylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isooctylamine, isononylamine, isodecylamine, isoundecylamine, isododecylamine, isopropylamine, sec-butylamine, sec-pentylamine, sec-hexylamine, sec-heptylamine, sec-octylamine, sec-nonylamine, sec-decylamine, sec-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine, benzylamine, o-cyanobenzylamine, m-cyanobenzylamine, o-chlorobenzylamine, m-chlorobenzylamine, p-chlorobenzylamine, o-methoxybenzylamine, m-methoxybenzylamine, p-methoxybenzylamine, o-nitrobenzylamine, m-nitrobenzylamine, p-nitrobenzylamine, o-methylbenzylamine, m-methylbenzylamine, p-methylbenzylamine, phenetylamine, N-methylbenzylamine, phenylamine, o-cyanophenylamine, m-cyanophenylamine, p-cyanophenylamine, o-chlorophenylamine, m-chlorophenylamine, p-chlorophenylamine, o-methoxyphenylamine, m-methoxyphenylamine, p-methoxyphenylamine, o-nitrophenylamine, m-nitrophenylamine, p-nitrophenylamine, o-methylphenylamine, m-methylphenylamine, p-methylphenylamine, N-methylphenylamine, diphenylamine, methyl azetidinecarboxylate hydrochloride, alanine methyl ester hydrochloride, asparagine methyl ester hydrochloride, dimethyl aspartate hydrochloride, S-benzylcysteine methyl ester hydrochloride, dimethyl glutamate hydrochloride, glutamine methyl ester hydrochloride, glycine methyl ester hydrochloride, histidine methyl ester hydrochloride, N,O-dibenzylhydroxylysine methyl ester hydrochloride, O-benzylhydroxyproline methyl ester hydrochloride, isoleucine methyl ester hydrochloride, leucine methyl ester hydrochloride, N-carbobenzyloxylysine methyl ester hydrochloride, methionine methyl ester hydrochloride, phenylalanine methyl ester hydrochloride, proline methyl ester hydrochloride, O-benzylserine methyl ester hydrochloride, O-benzylthreonine methyl ester hydrochloride, tryptophane methyl ester hydrochloride, O-benzyltyrosine methyl ester hydrochloride, valine methyl ester hydrochloride, naphthylalanine methyl ester hydrochloride, pipecolic acid methyl ester hydrochloride, N-carbobenzyloxyornithine methyl ester hydrochloride, ethyl (2-aminothiazol-4-yl)-2-methoxyiminoacetate, N,O-demethylhydroxylamin hydrochloride, and 1-methyl-1-phenylhyrazine.

Comparative Example 2

Synthesis of Boc-L-azetidinecarboxylic acid-n-butylamide Using the Mixed Acid Anhydride Mass Obtained According to Comparative Example 1

A well-dried reaction container equipped with a stirring apparatus, a thermometer, and a dropping funnel was purged with nitrogen, and Boc-L-azetidinecarboxylic acid 1 (10.00 g, 0.0497 mol), ethyl acetate (26 g) and N-methylmorpholine (5.53 g, 0.0547 mole) were added thereto at a room temperature and stirred and dissolved and after that, the inner temperature was cooled to −10° C. or lower. Isobutyl chlorocarbonate (6.79 g, 0.0497 mol) was dropwise added to the resultant mixture at an inner temperature of −5° C. in 1.5 hour. The obtained product was kept at the temperature for 1 hour and then, n-butylamine (3.63 g, 0.0497 mol) was dropwise added to the product in 1 hour at −5° C. or lower and the resultant product was kept at the temperature for 3 hours.

After completion of the reaction, ion-exchange water (30 g) was added and stirred at 10° C. or lower, settled and separated, and successively the obtained organic layer was washed with 1.8% hydrochloric acid (14 g), settled and separated at a room temperature and further the obtained organic layer was washed with an aqueous 2% sodium hydroxide solution (3.8 g), settled and separated at a room temperature. The obtained organic layer was washed with ion-exchange water (6 g) and separated from water and evaporated to obtain a pale yellowish liquid (11.96 g). The obtained liquid was subjected to silica gel column chromatography [silica gel 150 g; development solvent hexane/ethyl acetate (1:1) to (1:3)] to obtain an aiming product in form of a colorless transparent (8.01 g, LC purity 97.1%, yield: 60.7% based on "1").

Example 13

Synthesis of Boc-L-naphthylalanine N-methylbenzylamide 5

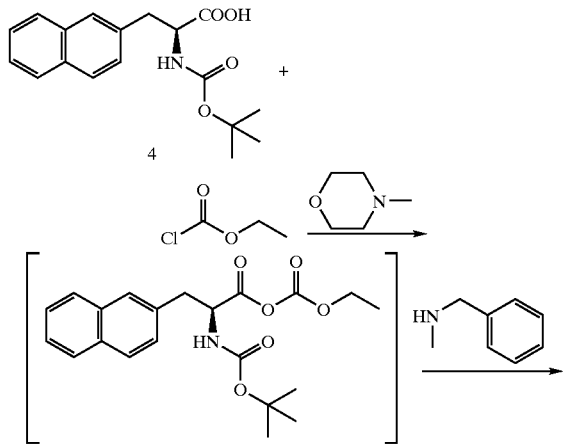

-continued

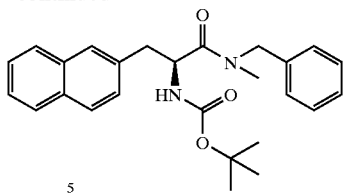

A substrate solution was produced by adding Boc-L-naphthylalanine 4 (10.00 g, 0.0314 mole) and ethyl acetate (26 g) at a room temperature and stirred to dissolving them. A well-dried reaction container equipped with a stirring apparatus, a thermometer, and a dropping funnel was purged with nitrogen, and ethyl chlorocarbonate (3.51 g, purity 97%, 0.0314 mol) and ethyl acetate (26 g) were added to the container and stirred and cooled to an inner temperature of −10°. Then, the substrate solution thus obtained and N-methylmorpholine (3.18 g, 0.0314 mol) were simultaneously but separaetely dropwise added in 45 minutes at an inner temperature of −5±2° C. and kept at the temperature for 30 minutes. Further, N-methylbenzylamine (3.80 g, 0.0314 mol) was dropwise added to the resultant solution in 20 minutes at −5° C. to 0° C. and the resultant solution was kept at the temperature for 3 hours. After completion of the reaction, 1% hydrochloric acid (22 g) was dropwise added at 10° C. or lower and after stirred for 10 minutes, settled and separated. The obtained organic layer was washed with ion-exchange water (15 g) at 5 to 10° C., settled and separated. The obtained organic layer was washed with an aqueous 5% sodium hydrogen carbonate solution (26 g) at 15 to 30° C., settled and separated. The obtained organic layer was washed with ion-exchange water (15 g) at 25 to 35° C., settled and separated. The obtained organic layer was evaporated to obtain a white solid substance (13.12 g). The content of the desired product was found 88.89% (by LC integrated surface percentage) and the yield was 89.89% (based on "4").

Example 13-2

Desired amide compounds are obtained in the same manner by using the following various kinds of amines in place of N-methylbenzylamine in Example 13: ammonia, methylamine, ethylamine, n-propylamine, n-butylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isooctylamine, isononlylamine, isodecylamine, isoundecylamine, isododecylamine, isopropylamine, sec-butylamine, sec-pentylamine, sec-hexylamine, sec-heptylamine, sec-octylamine, sec-nonylamine, sec-decylamine, sec-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine, benzylamine, o-cyanobenzylamine, m-cyanobenzylamine, o-chlorobenzylamine, m-chlorobenzylamine, p-chlorobenzylamine, o-methoxybenzylamine, m-methoxybenzylamine, p-methoxybenzylamine, o-nitrobenzylamine, m-nitrobenzylamine, p-nitrobenzylamine, o-methylbenzylamine, m-methylbenzylamine, p-methylbenzylamine, phenetylamine, N-methylbenzylamine, phenylamine, o-cyanophenylamine, m-cyanophenylamine, p-cyanophenylamine, o-chlorophenylamine, m-chlorophenylamine, p chlorophenylamine, o-methoxyphenylamine, m-methoxyphenylamine, p-methoxyphenylamine, o-nitrophenylamine, m-nitrophenylamine, p-nitrophenylamine, o-methylphenylamine, m-methylphenylamine, p-methylphenylamine, N-methylphenylamine, diphenylamine, methyl azetidinecarboxylate hydrochloride, alanine methyl ester hydrochloride, asparagine methyl ester hydrochloride, dimethyl aspartate hydrochloride, S-benzylcysteine methyl ester hydrochloride, dimethyl glutamate hydrochloride, glutamine methyl ester hydrochloride, glycine methyl ester hydrochloride, histidine methyl ester hydrochloride, N,O-dibenzylhydroxylysine methyl ester hydrochloride, O-benzylhydroxyproline methyl ester hydrochloride, isoleucine methyl ester hydrochloride, leucine methyl ester hydrochloride, N-carbobenzyloxylysine methyl ester hydrochloride, methionine methyl ester hydrochloride, phenylalanine methyl ester hydrochloride, proline methyl ester hydrochloride, O-benzylserine methyl ester hydrochloride, O-benzylthreonine methyl ester hydrochloride, tryptophane methyl ester hydrochloride, O-benzyltyrosine methyl ester hydrochloride, valine methyl ester hydrochloride, naphthylalanine methyl ester hydrochloride, pipecolic acid methyl ester hydrochloride, N-carbobenzyloxyornithine methyl ester hydrochloride, ethyl (2-aminothiazol-4-yl)-2-methoxyiminoacetate, N,O-demethylhydroxylamin hydrochloride, and 1-methyl-1-phenylhyrazine.

Example 14

Synthesis of Dipeptide 8

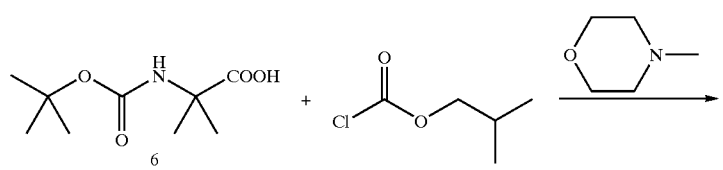

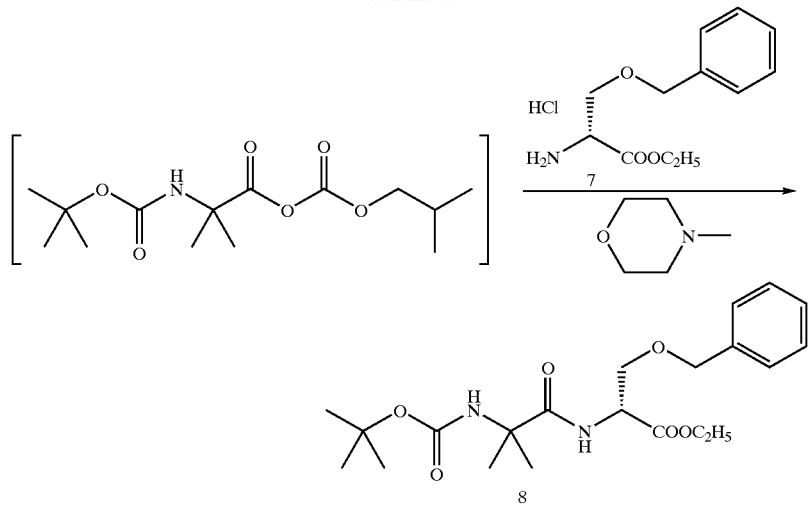

A substrate solution was prepared by adding N-methylmorpholine (5.69 g, 0.0542 mole) to Boc-2,2-dimethylglycine 6 (11.15 g, 0.0542 mol) and tetrahydrofuran (56 g) at a room temperature and dissolved under stirring. A well-dried reaction container equipped with a stirring apparatus, a thermometer, and a dropping funnel was purged with nitrogen, and isobutyl chlorocarbonate (7.56 g, 0.0542 mol) and tetrahydrofuran (70 g) were added to the container and stirred and the inner temperature thereof was cooled to −10° C. Then, the substrate solution thus prepared above was dropwise added in 1.5 hours at an inner temperature of −7±2° C. and kept at the temperature for 1 hour. Farther, O-benzylserine methyl ester hydrochloride 7 (13.97 g, 0.0539 mol) was added thereto at −7±2° C. inner temperature to the resultant solution and N-methylmorpholine (6.10 g, 0.0593 mol) was dropwise added in 45 minutes at an inner temperature of −7±2° C. and the resultant solution was kept at the temperature for 2 hours.

After completion of the reaction, ethyl acetate (57 g) was added at −5 to 5° C., and 1% hydrochloric acid (57 g) was dropwide added at −5 to 5° C. and stirred for 10 minutes, settled and separated. The obtained organic layer was washed with ion-exchange water (56 g), settled and separated. The obtained organic layer was washed with an aqueous 5% sodium hydrogen carbonate solution (28 g) at 10 to 30° C., settled and separated. After that, the organic layer was washed with ion exchange water (28 g) at 10 to 30° C., settled and separated to obtain a solution (184.22 g) containing desired product "8". The content of the product "8" was found 11.3% by (LC-IS method) and the yield was 94.0% (based on "7").

Example 14-2

Desired amide compounds are obtained in a similar manner by using the following various kinds of amines in place of O-benzyl-D-serine methyl ester hydrochloride in Example 14: ammonia, methylamine, ethylamine, n-propylamine, n-butylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isooctylamine, isononylamine, isodecylamine, isoundecylamine, isododecylamine, isopropylamine, sec-butylamine, sec-pentylamine, sec-hexylamine, sec-heptylamine, sec octylamine, sec-nonylamine, sec decylamine, see-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine, benzylamine, o-cyanobenzylamine, m-cyanobenzylamine, o-chlorobenzylamine, m-chlorobenzylamine, p-chlorobenzylamine, o-methoxybenzylamine, m-methoxybenzylamine, p-methoxybenzylamine, o-nitrobenzylamine, m-nitrobenzylamine, p-nitrobenzylamine, o-methylbenzylamine, m-methylbenzylamine, p-methylbenzylamine, phenetylamine, N-methylbenzylamine, phenylamine, o-cyanophenylamine, m-cyanophenylamine, p-cyanophenylamine, o-chlorophenylamine, m-chlorophenylamine, p-chlorophenylamine, o-methoxyphenylamine, m-methoxyphenylamine, p-methoxyphenylamine, o-nitrophenylamine, m-nitrophenylamine, p-nitrophenylamine, o-methylphenylamine, m-methylphenylamine, p-methylphenylamine, N-methylphenylamine, diphenylamine, methyl azetidinecarboxylate hydrochloride, alanine methyl ester hydrochloride, asparagine methyl ester hydrochloride, dimethyl aspartate hydrochloride, S-benzylcysteine methyl ester hydrochloride, dimethyl glutamate hydrochloride, glutamine methyl ester hydrochloride, glycine methyl ester hydrochloride, histidine methyl ester hydrochloride, N,O-dibenzylhydroxylysine methyl ester hydrochloride, O-benzylhydroxyproline methyl ester hydrochloride, isoleucine methyl ester hydrochloride, leucine methyl ester hydrochloride, N-carbobenzyloxylysine methyl ester hydrochloride, methionine methyl ester hydrochloride, phenylalanine methyl ester hydrochloride, proline methyl ester hydrochloride, O-benzylthreonine methyl ester hydrochloride, tryptophane methyl ester hydrochloride, O-benzyltyrosine methyl ester hydrochloride, valine methyl ester hydrochloride, naphthylalanine methyl ester hydrochloride, pipecolic acid methyl ester hydrochloride, N-carbobenzyloxyornithine methyl ester hydrochloride, ethyl (2-aminothiazol-4-yl)-2-methoxyiminoacetate, N,O-

Example 15

Synthesis of Ethyl N-Boc-L-alanyl-(2-aminothiazole-4-yl)-2-methoxyiminoacetate (Z isomer) 11

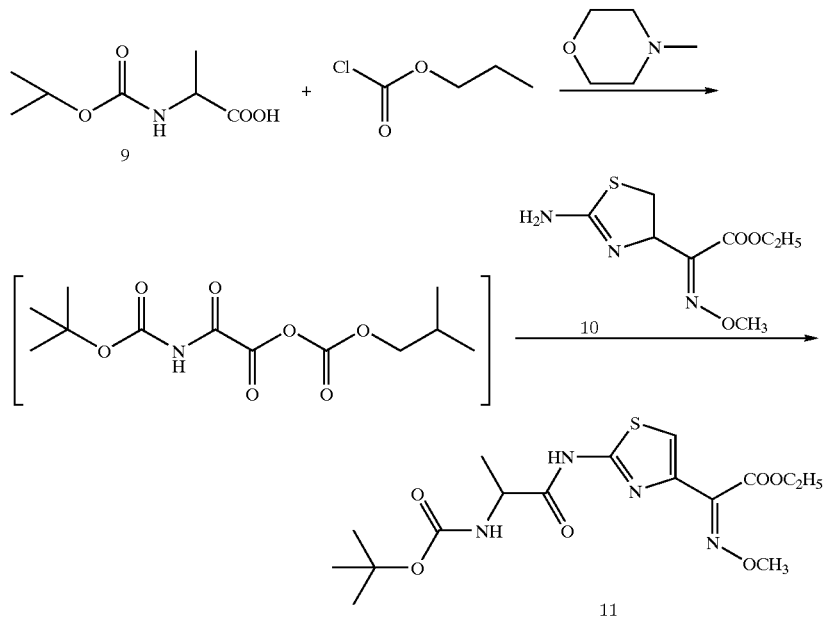

A substrate solution was prepared by adding N-methylmorpholine (5.16 g, 0.0510 mole) to Boc-L-alanine 9 (9.64 g, 0.0510 mol) and tetrahydrofuran (24 g) at a room temperature and mixing under stirring. A well-dried reaction container equipped with a stirring apparatus, a thermometer and a dropping funnel was purged with nitrogen, and isobutyl chlorocarbonate (7.10 g, 0.0510 mol) and tetrahydrofuran (24 g) were added to the container and stirred and cooled to an inner temperature of −10° C. Then, the substrate solution thus prepared was dropwise added there to at an inner temperature of −5° C. or lower and kept at −10 to −5° C. for 30 minutes. Further, the solution of ethyl (2-aminothiazole-4-yl)-2-methoxyiminoacetate (Z isomer) 10 (8.76 g, 0.0382 mole) in tetrahydrofuran (66 g), prepared beforehand, was dropwise added to the resultant solution at an inner temperature of 20±2° C. in 2 hours and the resultant solution was kept at the temperature for 24 hours.

After completion of the reaction, 0.3% hydrochloric acid (8.8 g) was added dropwise at 10° C. or lower and after stirring at the same temperature, settled and separated. The obtained organic layer was washed with 20% saline water (8.8 g) at 5 to 10° C., settled and separated, and then the organic layer was mixed with ion-exchange water (18 g) and an aqueous 6% sodium hydrogen carbonate solution (8.8 g) at 30° C. or lower and stirred, settled and separated. The obtained organic layer was washed with 20% saline water (8.8 g) at 30° C. or lower, settled and separated, and evaporated to obtain a solution (40.73 g) containing the desired product 11. The content of the desired product 11 was 33.0% (by LC-IS method) and the yield was 88.0% (based on "10").

Example 15-2

Desired amide compounds are obtained in a similar manner by using the various kinds of amines as follows in place of (2-aminothiazole-4-yl)-2-methoxyimionoacetate (Z isomer) in Example 15: ammonia, methylamine, ethylamine, n-propylamine, n-butylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isooctylamine, isononylamine, isodecylamine, isoundecylamine, isododecylamine, isopropylamine, sec-butylamine, sec-pentylamine, sec-hexylamine, sec-heptylamine, sec-octylamine, sec-nonylamine, sec-decylamine, sec-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine, benzylamine, o-cyanobenzylamine, m-cyanobenzylamine, o-chlorobenzylamine, m-chlorobenzylamine, p-chlorobenzylamine, o-methoxybenzylamine, m-methoxybenzylamine, p-methoxybenzylamine, o-nitrobenzylamine, m-nitrobenzylamine, p-nitrobenzylamine, o-methylbenzylamine, m-methylbenzylamine, p-methylbenzylamine, phenetylamine, N-methylbenzylamine, phenylamine, o-cyanophenylamine, m-cyanophenylamine, p-cyanophenylamine, o-chlorophenylamine, m-chlorophenylamine, p-chlorophenylamine, o-methoxyphenylamine, m-methoxyphenylamine, p-methoxyphenylamine, o-nitrophenylamine, m-nitrophenylamine, p-nitrophenylamine, o-methylphenylamine, m-methylphenylamine, p-methylphenylamine, N-methylphenylamine, diphenylamine, methyl azetidinecarboxylate hydrochloride, alanine methyl ester hydrochloride, asparagine methyl ester hydrochloride, dimethyl aspartate hydrochloride, S-benzylcysteine methyl ester hydrochloride, dimethyl glutamate hydrochloride, glutamine methyl ester hydrochloride, glycine methyl ester hydrochloride, histidine methyl ester hydrochloride, N,O- dibenzylhydroxylysine methyl ester hydrochloride, O-benzylhydroxyproline methyl ester hydrochloride, isoleucine methyl ester hydrochloride, leucine methyl ester hydrochloride, N-carbobenzyloxylysine methyl ester hydrochloride, methionine methyl ester hydrochloride, phenylalanine methyl ester hydrochloride, proline methyl ester hydrochloride, O-benzylserine methyl ester hydrochloride, O-benzylthreonine methyl ester hydrochloride, tryptophane methyl ester hydrochloride, O-benzyltyrosine methyl ester hydrochloride, valine methyl ester hydrochloride, naphthylalanine methyl ester hydrochloride, pipecolic acid methyl ester hydrochloride, N-carbobenzyloxyornithine methyl ester hydrochloride, N,O-demethylhydroxylamin hydrochloride, and 1-methyl-1-phenylhyrazine.

Example 16

Synthesis of N-benzylacetamide

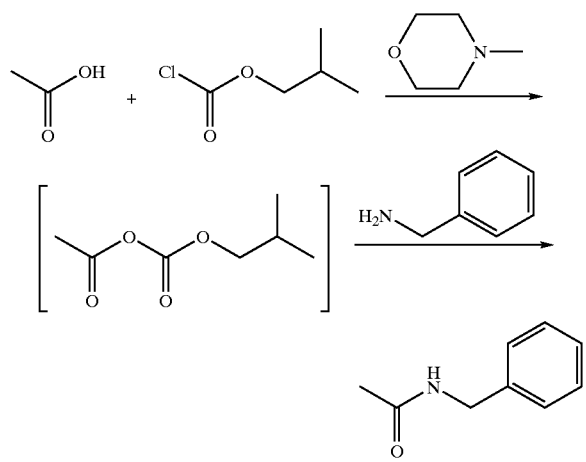

A substrate solution was prepared by adding N-methylmorpholine (7.08 g, 0.0700 mole) to acetic acid (4.20 g, 0.0700 mol) and ethyl acetate (11 g) at a room temperature and mixing under stirring. A well-dried reaction container equipped with a stirring apparatus, a thermometer, and a dropping funnel was purged with nitrogen, and isobutyl chlorocarbonate (9.56 g, 0.0700 mol) and ethyl acetate (10 g) were added to the container and stirred and cooled to an inner temperature of −10° C. Then, the substrate solution thus prepared was dropwise added at an inner temperature of −6 to −2° C. in 2 hours, and kept at the temperature for 30 minutes. Further, benzylamine (7.50 g, 0.0700 mol) was dropwise added to the solution in 1 hour at −4 to 0° C. and the resultant solution was kept at the temperature for 3 hours.

After completion of the reaction, 1% hydrochloric acid (23 g) was dropwide added at 10° C. or lower and after stirred for 30 minutes, settled and separated. The obtained organic layer was washed with 9% salt water (7 g) at 5 to 10° C., settled and separated. The obtained organic layer was washed with an aqueous 5% sodium hydrogen carbonate solution (11.8 g) at 15 to 30° C., settled and separated After that, the organic layer was washed with ion-exchange water (6 g) at 25 to 35° C., settled and separated. The obtained organic layer was evaporated to obtain a solution (10.04 g) of a desired pale yellowish transparent solution or white solid. The content was found 86.5% by gas chromatography analysis. The pure product yield was 8.68 g (yield 87.8% based on acetic acid). The content of impurities are as follows; diisobutylcarbonate: 2.0%, and N-isobutyloxycarbonyl)-benzylamine: 2.5%.

Example 16-2

Desired amide compounds are obtained in a similar manner by using various kinds of amines as follows in place of benzylamine in Example 16: ammonia, methylamine, ethylamine, n-propylamine, n-butylamine, n-pentylamine, n-hexylamine, n-heptylamine, n-octylamine, n-nonylamine, n-decylamine, n-undecylamine, n-dodecylamine, isobutylamine, isopentylamine, isohexylamine, isoheptylamine, isooctylamine, isononylamine, isodecylamine, isoundecylamine, isododecylamine, isopropylamine, sec-butylamine, sec-pentylamine, sec-hexylamine, sec-heptylamine, sec-octylamine, sec-nonylamine, sec-decylamine, sec-undecylamine, sec-dodecylamine, tert-butylamine, tert-pentylamine, tert-hexylamine, tert-heptylamine, tert-octylamine, tert-nonylamine, tert-decylamine, tert-undecylamine, tert-dodecylamine, dimethylamine, diethylamine, di-n-propylamine, di-n-butylamine, di-n-pentylamine, di-n-hexylamine, di-n-heptylamine, di-n-octylamine, di-n-nonylamine, di-n-decylamine, di-n-undecylamine, di-n-dodecylamine, o-cyanobenzylamine, m-cyanobenzylamine, o-chlorobenzylamine, m-chlorobenzylamine, p-chlorobenzylamine, o-methoxybenzylamine, m-methoxybenzylamine, p-methoxybenzylamine, o-nitrobenzylamine, m-nitrobenzylamine, p-nitrobenzylamine, o-methylbenzylamine, m-methylbenzylamine, p-methylbenzylamine, phenetylamine, N-methylbenzylamine, phenylamine, o-cyanophenylamine, m-cyanophenylamine, p-cyanophenylamine, o-chlorophenylamine, m-chlorophenylamine, p-chlorophenylamine, o-methoxyphenylamine, m-methoxyphenylamine, p-methoxyphenylamine, o-nitrophenylamine, m-nitrophenylamine, p-nitrophenylamine, o-methylphenylamine, m-methylphenylamine, p-methylphenylamine, N-methylphenylamine, diphenylamine, methyl azetidinecarboxylate hydrochloride, alanine methyl ester hydrochloride, asparagine methyl ester hydrochloride, dimethyl aspartate hydrochloride, S-benzylcysteine methyl ester hydrochloride, dimethyl glutamate hydrochloride, glutamine methyl ester hydrochloride, glycine methyl ester hydrochloride, histidine methyl ester hydrochloride, N,O-dibenzylhydroxylysine methyl ester hydrochloride, O-benzylhydroxyproline methyl ester hydrochloride, isoleucine methyl ester hydrochloride, leucine methyl ester hydrochloride, N-carbobenzyloxylysine methyl ester hydrochloride, methionine methyl ester hydrochloride, phenylalanine methyl ester hydrochloride, proline methyl ester hydrochloride, O-benzylserine methyl ester hydrochloride, O-benzylthreonine methyl ester hydrochloride, tryptophane methyl ester hydrochloride, O-benzyltyrosine methyl ester hydrochloride, valine methyl ester hydrochloride, naphthylalanine methyl ester hydrochloride, pipecolic acid methyl ester hydrochloride, N-carbobenzyloxyornithine methyl ester hydrochloride, ethyl (2-aminothiazol-4-yl)-2-methoxyiminoacetate, N,O-demethylhydroxylamine hydrochloride, and 1-methyl-1-phenylhyrazine.

Example 16–3

Desired amide compounds are obtained in a similar manner by using various kinds of carboxylic acids as follows in place of acetic acid in Example 16: formic acid, propionic acid, butanoic acid, varelic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, isobutanoic acid, isovaleric acid, 4-methylpentanoic acid, 5-methylhexhanoic acid, 6-methylheptanoic acid, 7-methyloctanoic acid, 8-methylnonanoic acid, 9-methyldecaonic acid, 2-methylbutanoic acid, 2-methylpentanoic acid, 2-methylhexanoic acid, 2-methylheptanoic acid, 2-methyloctanoic acid, 2-methylnonanoic acid, 2-methyldecanoic acid, pivalic acid, cyclohexanecarboxlic acid, O-benzyl-2-hydroxypentanoic acid, O-benzyl-2-hydroxy-cyclohexanecarboxylic acid, 3-phenylpropionic acid, O-benzyl-1-hydroxy-1-phenylacetic acid, benzoic acid, o-methylbenzoic acid, m-methylbenzoic acid, p-methylbenzoic acid, o-phenylbenzoic acid, m-phenylbenzoic acid, p-phenylbenzoic acid, O-benzyl-o-hydroxybenzoic acid, O-benzyl-m-hydroxybenzoic acid, O-benzyl-p-hydroxybenzoic acid, furancarboxylic add, tetrahydrofurancarboxylic acid, thiophenecarboxylic acid.

Comparative Example 3

Comparative Example for Example 16

A well-dried reaction container equipped with a stirring apparatus, a thermometer and a dropping funnel was purged with nitrogen, and acetic acid 1 (4.20 g, 0.0700 mol), ethyl acetate (21 g) and N-methylmorpholine (7.08 g, 0.0700 mole) were added thereto at a room temperature and mixed under stirring and after that, the inner temperature was cooled to −10° C. or lower. Then, isobutyl chlorocarbonate (9.56 g, 0.0700 mol) was dropwise added to the resultant mixture at an inner temperature of −5 to −3° C. in 2 hour. The obtained product was kept at the temperature for 30 minutes and then, benzylamine (7.50 g, 0.0700 mol) was dropwise added thereto in 1 hour at −4 to 0° C. and the resultant product was kept at the temperature for 3 hours.

After completion of the reaction, 1% hydrochloric acid (23 g) was added at 10° C. or lower and stirred for 30 minutes and the solution was settled and separated. The obtained organic layer was washed with 9% salt water (7 g) at 5 to 10° C., settled and separated. The obtained organic layer was washed with an aqueous 5% sodium hydrogen carbonate solution (11.8 g) at 15 to 30° C., settled and separated, and the resultant organic layer was washed with ion-exchange water (6 g) at 25 to 35° C., settled and separated. The finally obtained organic layer was evaporated to obtain a pale yellowish solution (12.60 g) of the desired product. The content was found 46.5% by gas chromatography analysis. The pure product yield was 5.86 g (yield ratio 59.3% on the basis of acetic acid). The impurity contents were as follows: diisobutylcarbonate: 9.4%, and N-(isobutyloxycarbonyl)-benzylamine: 33.9%.

What is claimed is:

1. A method for producing a mixed acid anhydride of formula (1):

$$R^1C(O)OY(O)_n(R^2)_p \qquad (1)$$

wherein $R^1$, $R^2$, Y, n and p denote the same as defined below, which comprises adding a carboxylic acid of formula (2);

$$R^1COOH \qquad (2)$$

wherein $R^1$ denotes a hydrogen atom, an optionally substituted saturated or unsaturated hydrocarbyl group, or an optionally substituted hetero ring, and an organic base comprising N-methylmorpholine to a solution of a carboxylic acid activating agent of formula (3);

$$(R^2)_pY(O)_nX \qquad (3)$$

wherein $R^2$ denotes an optionally substituted alkyl group, an optionally substituted aryl group, an optionally substituted chain or cyclic alkoxy group, or an optionally substituted aryloxy group, Y denotes a carbon atom, a phosphorus atom, or a sulfur atom, X denotes a fluorine atom, a chlorine atom, a bromine atom, an iodine atom, a cyano group or a group of formula:

$$(R^2)_pY(O)_nO—,$$

wherein $R^2$ is the same as defined above, n and p are an integer of 1 or 2; and when Y is a carbon atom, n=1 and p=1, when Y is a phosphorous atom, n=1 and p=2, and when Y is sulfur atom, n=2 and p=1 and $R^2$ denotes an optionally substituted alkyl or aryl group.

2. A method according to claim 1, wherein $R^1$ denotes a hydrogen atom, a straight, branched or cyclic (C1–C17) alkyl group, a (C2–C5)alkenyl or (C5–C6)cycloalkenyl group, a (C3–C4) alkynyl group, a phenyl, tolyl, biphenyl or naphthyl group, an aralkyl, arylalkenyl or arylalkynyl group, a pyridyl group, a 1,3-oxazole group, a 1,3-thiazole group, a furyl group, a tetrahydrofuryl group, a thienyl group, an imidazole or (C2–C11) alkyleneimine group of which nitrogen atoms are protected by a protecting group, wherein said groups other than hydrogen atom may be substituted with (a) a hydroxy group or a halogen atom, or (b) an amino group of formula:

$$R^{11}R^{12}N— \text{ and}$$

optionally further with at least one group selected from a carbamoyl group, a methylmercapto group, a 4-pyrimidinone-3-yl group, an alkyl(C1–C3) dithio group, of which alkyl is substituted with a protected amino and carboxyl groups, a mercapto, guanidyl, carboxyl, hydroxy or imidazolyl group, wherein $R^{11}$ represents a hydrogen atom or an amino-protecting group, $R^{12}$ represents an amino-protecting group, or a group of formula: $R^{13}$—CO, wherein $R^{13}$ represents a saturated or unsaturated hydrocarbyl group or a hetero ring, which may be substituted with (c) a hydroxy group, or a halogen atom, or a group of formula: $R^{14}R^{15}N—$ and optionally further with at least one group selected from a carbamoyl group, a methylmercapto group, an alkyl(C1–C3) dithio group, of which alkyl is substituted with an amino and carboxyl groups, an amino, mercapto, guanidyl, carboxyl, hydroxy, imidazolyl group, wherein $R^{14}$ is an amino-protecting group, and $R^{15}$ represents a hydrogen atom, a saturated or unsaturated hydrocarbyl group, a hetero ring or an amino-protecting group, provided that said amino, mercapto, guanidyl, carboxyl, hydroxy and imidazolyl groups which may be present in $R^1$, $R^2$, and substituent groups contained therein are in a protected form, $R^2$ denotes a chain, branched or cyclic (C1–C6) alkyl group, which may be substituted with a halogen atom, a phenyl which may be substituted with a halogen or (C1–C3) alkyl group, a chain or cyclic (C1–C6) alkoxy group, or a phenoxy group which may be substituted with a halogen or C1–C3 alkyl group.

3. A method according to claim 2, wherein $R^1$ represents a group of formula (6):

$$R^{11}R^{12}N\text{—}A\text{—} \tag{6}$$

wherein $R^{11}$ and $R^{12}$ are the same as defined in claim 2, and A represents an alkylene group, an alkenylene group, an alkynylene group, an arylene group, an aralkylene group, an arylalkenylene group, arylalkynylene group, an oxazole ring, a thiazole ring, or an imidazole ring.

4. A method for producing a mixed acid anhydride of formula (1):

$$RC(O)OY(O)_n(R^2)_p \tag{1}$$

wherein $R^1$, $R^2$, Y, n and p denote the same as defined below, which comprises adding a carboxylic acid of formula (2):

$$R^1COOH \tag{2}$$

wherein $R^1$ denotes a hydrogen atom, a straight, branched or cyclic (C1–C18) alkyl group, a (C2–C5) alkenyl or (C5–C6) cycloalkenyl group, a (C3–C4) alkynyl group, a phenyl, tolyl, biphenyl or naphthyl group, an aralkyl, arylalkenyl or arylalkynyl group, a pyridyl group, a 1,3-oxazole group, a 1,3-thiazole group, a furyl group, a tetrahydrofuryl group, a thienyl group, an irnidazole or (C2–C11) alkyleneimine group of which nitrogen atoms are protected by a protecting group, wherein said groups other than hydrogen atom may be substituted with (c) a hdyroxy group or a halogen atom, or (d) an amino group of formula:

$$R^{11}R^{12}N\text{— and}$$

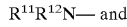

optionally further with at least one group selected from a carbamoyl group, a methylmercapto group, a 4-pyrimidinone-3-yl group, an alkyl (C1–C3) dithio group, of which alkyl is substituted with an amino and carboxyl groups, a mercapto, guanidyl, carboxyl, hydroxy or imidazolyl group, wherein $R^{11}$ represents a hydrogen atom or an amino-protecting group, $R^{12}$ represents an amino-protecting group, or a group of formula: $R^{13}$—CO, wherein $R^{13}$ represents a saturated or unsaturated hydrocarbyl group or a hetero ring, which may be substituted with (c) a hydroxy group, or a halogen atom, or a group of formula: $R^{14}R^{15}N$— and optionally further with at least one group selected from a carbamoyl group, a methylmercapto group, an alkyl (C1–C3) dithio group, of which alkyl is substituted with an amino and carboxyl groups, an amino, mercapto, guanidyl, carboxyl, hydroxy, or imidazolyl group, wherein $R^{14}$ is an amino-protecting group, and $R^{15}$ represents a hydrogen atom, a saturated or unsaturated hydrocarbyl group, a hetero ring or an amino-protecting group, and an organic base comprising N-methylmorpholine to a solution of a carboxylic acid activating agent of formula (3):

$$(R^2)_pY(O)_nX \tag{3}$$

wherein $R^2$ denotes a chain, branched or cyclic (C1–C6) alkyl group, which may be substituted with a halogen atom, a phenyl which may be substituted with a halogen or (C1–C3) alkyl group, a chain or cyclic (C1–C6) alkoxy group, or a phenyl group which may be substituted with a halogen or C1–C3 alkyl group, Y denotes a carbon atom, a phophorus atom, or a sulfur atom, X denotes a fluorine atom, a chlorine atom, a bromine atom, an iodine atom, a cyano group or a group of formula:

$$(R^2)_pY(O)_nO\text{—},$$

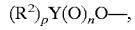

wherein $R^2$ is the same as defined above, n and p are an integer of 1 or 2; and when Y is a carbon atom, n=1 and p=1, when Y is a phosphorous atom, n=1 and p=2, and when Y is sulfur atom, n=2 and p=1 and $R^2$ denotes an optionally substituted alkyl or aryl group, provided that said amino, mercapto, guanidyl, carboxyl, hydroxy and imidazolyl groups which may be present in $R^1$ and $R^2$ and substituent groups contained therein are in a protected form.

5. A method according to claim 4, wherein said carboxylic acid of formula (1) is an α-amino acid derivative of formula (7):

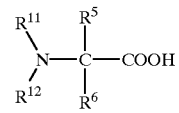

$$\begin{array}{c} R^{11} \quad R^5 \\ \diagdown \quad | \\ N\text{—}C\text{—}COOH \\ \diagup \quad | \\ R^{12} \quad R^6 \end{array} \tag{7}$$

wherein $R^5$ and $R^6$ represent a hydrogen atom or a saturated or unsaturated hydrocarbyl group or a hetero ring, both of which may be each substituted with (a) a hydroxy group or a halogen atom, or (b) at least one group selected from a carbamoyl group, a methylmercapto group, an alkyl (C1–C3) dithio group, of which alkyl is substituted with a protected amino and carboxyl groups, and an amino, mercapro, guanidyl, carboxyl, hydroxy or imidazolyl group, $R^{11}$ is a hydrogen atom or an amino-protecting group, $R^{12}$ represents an amino-protecting group or a group of formula: $R^{13}CO—$, wherein $R^{13}$ represents a saturated or unsaturated hydrocarbyl group or a hetero ring, which may be substituted with (c) a hydroxy or a halogen atom, or (e) a group of formula: $R^{14}R^{15}N—$ and optionally further with at least one group selected from a carbamoyl group, a methylmercapto group, alkyl (C1–C3) dithio group, of which alkyl is substituted with a protected amino and carboxyl groups, an amino, mercapto, guanidyl, carboxyl, hydroxy, or imidazolyl group, wherein $R^{14}$ is an amino-protecting group, $R^{15}$ represents a hydrogen atom or an amino-protecting group, and $R^{11}$ and $R^{12}$, and $R^{14}$ and $R^{15}$ may independently form an alkyleneimine group, or a 4-pyrimidinone-3-yl group, provided that said amino, mercapto, guanidyl, carboxyl, hydroxy and imidazolyl groups which may be present in $R^{11}$, $R^{12}$, $R^5$ and $R^6$ or substituent groups contained therein are in a protected form.

6. A method for producing a mixed acid anhydride of formula (1):

$$R^1C(O)OY(O)_n(R^2)_p \quad (1)$$

wherein $R^1$, $R^2$, Y, n and p denote the same as defined below, which comprises adding a carboxylic acid of formula (2):

$$R^1COOH \quad (2)$$

wherein $R^1$ denotes a group of formula (6):

$$R^{11}R^{12}N—A— \quad (6)$$

wherein $R^{11}$ represents a hydrogen atom or an amino-protecting group, and $R^{12}$ represents an amino-protecting group, or a group of formula: $R^{13}—CO$, wherein $R^{13}$ represents a saturated or unsaturated hydrocarbyl group or a hetero ring, which may be substituted with a hydroxy group, or a halogen atom, or a group of formula: $R^{14}R^{15}N—$ and optionally further with at least one group selected from a carbamoyl group, a methylmercapto group, an alkyl (C1–C3) dithio group, of which alkyl is substituted with an amino and carboxyl groups, an amino, mercapto, guanidyl, carboxyl, hydroxy, or imidazolyl group, wherein $R^{14}$ is an amino-protecting group, and $R^{15}$ represents a hydrogen atom, a saturated or unsaturated hydrocarbyl group, a hetero ring or an amino-protecting group, A represents an alkylene group, an alkenylene group, an alkynylene group, an arylene group, an aralkylene group, an arylalkenylene group, an arylalkynylene group, an oxazole ring, a thiazole ring, or an imidazole ring, and an organic base comprising N-methylmorpholine to a solution of a carboxylic acid activating agent of formula (3):

$$(R^2)_pY(O)_nX \quad (3)$$

wherein $R^2$ denotes a chain, branched or cyclic (C1–C6) alkyl group, which may be substituted With a halogen atom, a phenyl which may be substituted with a halogen or (C1–C3) alkyl group, a chain or cyclic (C1–C6) alkoxy group, or a phenoxy group which may be substituted with a halogen or C1–C3 alkyl group, Y denotes a carbon atom, a phosphorus atom, or a sulfur atom, X denotes a fluorine atom, a chlorine atom, a bromine atom, an iodine atom, a cyano group or a group of formula:

$$(R^2)_pY(O)_nO—,$$

wherein R is the same as defined above, n and p are an integer of 1 or 2; and when Y is a carbon atom, n=1 and p=1, when Y is a phosphorous atom, n=1 and p=2, and when Y is sulfur atom, n=2 and p=1 and $R^2$ denotes an optionally substituted alkyl or aryl group, provided that said amino, mercapto, guanidyl, carboxyl, hydroxy and imidazolyl groups which may be present in $R^1$ and $R^2$ and substituent groups contained therein are in a protected form.

7. A method according to claim 5, wherein Y represents a carbon atom, n=1 and p=1.

8. A method for producing a mixed acid anhydride of formula (1):

$$R^1C(O)OY(O)_n(R^2)_p \quad (1)$$

wherein $R^1$, $R^2$, Y, n and p denote the same as defined below, which comprises adding a carboxylic acid of formula (2):

$$R^1COOH \quad (2)$$

wherein $R^1COOH$ is a cyclic α-amino acid derivative of formula (8):

(8)

wherein $R^6$ represents a hydrogen atom or a saturated or unsaturated hydrocarbyl group or a hetero ring, both of which may be substituted with (a) a hydroxy group or a halogen atom, or (b) at least one group selected from a carbamoyl group, a methylmercapto group, an alkyl (C1–C3) dithio group, of which alkyl is substituted with a protected amino and carboxyl groups, and an amino, mercapto, guanidyl, carboxyl, hydroxy or imidazolyl group, $R^{12}$ represents an amino-protecting group or a group of formula: $R^{13}CO—$, wherein $R^{13}$ represents a saturated or unsaturated hydrocarbyl group or a hetero ring, which may be substituted with (c) a hydroxy or a halogen atom, or (a) a group of formula: $R^{14}R^{15}N—$ and optionally further with at least one group selected from a carbamoyl group, a methylmercapto group, alkyl (C1–C3) dithio group, of which alkyl is substituted with a protected amino and carboxyl groups, an amino, mercapto, guanidyl, carboxyl, hydroxy, or imidazolyl group, wherein $R^{14}$ an amino-protecting group, $R^{15}$ represents a hydrogen atom or an amino-protecting group, and $R^{14}$ and $R^{15}$ may form an alkyleneimine group, or a 4-pyrimidinone-3-yl group, provided that said amino, mercapto, guanidyl, carboxyl, hydroxy and imidazolyl groups which may be present in $R^{12}$, $R^6$ or substituent groups contained therein are in a protected form, and m denotes an integer from 1 to 10, and an organic base to a solution of a carboxylic acid activating agent of formula (3):

$$(R^2)_p Y(O)_n X \qquad (3)$$

wherein R2 denotes
a chain, branched or cyclic (C1–C6) alkyl group, which may be substituted with a halogen atom,
a phenyl which may be substituted with a halogen or (C1–C3) alkyl group,
a chain or cyclic (C1–C6) alkoxy group, or
a phenyl group which may be substituted with a halogen or C1–C3 alkyl group,
Y denotes a carbon atom, a phophorus atom, or a sulfur atom,
X denotes a fluorine atom, a chlorine atom, a bromine atom, an iodine atom, a cyano group or a group of formula:

$$(R^2)_p Y(O)_n O\text{—},$$

wherein $R^2$ is the same as defined above, n and p are integers of 1 or 2; and when Y is a carbon atom, n=1 and p=1, when Y is a phosphorous atom, n=1 and p=2, and when Y is sulfur atom, n=2 and p=1 and $R^2$ denotes a chain, branched or cyclic (C1–C6) alkyl group, which may be substituted with a halogen atom, or a phenyl which may be substituted with a halogen or (C1–C3) alkyl group.

9. A method according to claim 1, wherein $R^1$ denotes a hydrogen atom, a straight, branched or cyclic (C1–C18)alkyl group, a (C2–C5)alkenyl or (C5–C6)cycloalkenyl group, a (C3–C4) alkynyl group, a phenyl, tolyl, biphenyl or naphthyl group, an aralkyl, arylalkenyl or arylalkynyl group, a pyridyl group, a 1,3-oxazole group, a 1,3-thiazole group, a furyl group, a tetrahydrofuryl group, a thienyl group, an imidazole or (C2–C11)alkyleneimine group of which nitrogen atoms are protected by a protecting group, wherein said groups other than hydrogen atom may be substituted with
(a) a hydroxy group or a halogen atom, or
(b) an amino group of formula:

$R^{11}R^{12}N$— and optionally further with at least one group selected from
a carbamoyl group, a methylmercapto group, a 4-pyrimidinone-3-yl group, an alkyl(C1–C3) dithio group, of which alkyl is substituted with a protected amino and carboxyl groups, a mercapto, guanidyl, carboxyl, hydroxy or imidazolyl group, wherein $R^{11}$ represents a hydrogen atom or an amino-protecting group,
$R^{12}$ represents an amino-protecting group, or a group of formula: $R^{13}$—CO,
wherein $R^{13}$ represents a saturated or unsaturated hydrocarbyl group or a hetero ring, which may be substituted with (c) a hydroxy group, or a halogen atom, or a group of formula: $R^{14}R^{15}N$— and optionally further with at least one group selected from
a carbamoyl group, a methylmercapto group, an alkyl (C1–C3) dithio group, of which alkyl is substituted with an amino and carboxyl groups, an amino, mercapto, guanidyl, carboxyl, hydroxy, or imidazolyl group,
wherein $R^{14}$ is an amino-protecting group, and
$R^{15}$ represents a hydrogen atom, a saturated or unsaturated hydrocarbyl group, a hetero ring or an amino-protecting group,
provided that said amino, mercapto, guanidyl, carboxyl, hydroxy and imidazolyl groups which may be present in $R^1$, $R^2$, and substituent groups contained therein are in a protected form,
$R^2$ denotes a chain, branched or cyclic (C1–C6) alkyl group, which may be substituted with a halogen atom, a phenyl which may be substituted with a halogen or (C1–C3) alkyl group, a chain or cyclic (C1–C6) alkoxy group, or a phenoxy group which may be substituted with a halogen or C1–C3 alkyl group, provided that the protecting group of the protected amino group, and the amino-protecting group is t-butyloxycarbonyl group.

10. A method according to claim 2 or 4, wherein the base and the carboxylic acid are simultaneously added.

11. The method according to claim 1, 4, 6, 5, or 8, wherein said carboxylic acid activating agent of formula (3) is an acid chloride.

12. The method according to claim 1, 4, 6, 5, or 8, wherein the amount of the organic base is 0.9 to 2 moles per mol of said carboxylic acid in the production of the mixed acid anhydride of formula (1).

13. The method according to claim claim 1, 4, 6, 5, or 8, wherein the amount of the carboxylic acid activating agent is 0.95 to 1.05 moles per mol of the carboxylic acid of formula (2).

14. The method according to claim claim 1, 4, 6, 5, or 8, wherein the amount of the organic base is 0.95 to 1.05 mol per mol of the carboxylic acid of formula (2).

15. The method according to claim claim 1, 4, 6, 5, or 8, wherein the amount of the organic base per mol of the carboxylic acid of formula (2) is substantially equimolar.

16. The method according to claim claim 1, 4, 6, 5, or 8, wherein the base and the carboxylic acid are simultaneously added.

* * * * *